United States Patent [19]
Adair

[11] Patent Number: 5,643,175
[45] Date of Patent: *Jul. 1, 1997

[54] STERILIZABLE ENDOSCOPE WITH SEPARABLE DISPOSABLE TUBE ASSEMBLY

[76] Inventor: Edwin L. Adair, 317 Paragon Way, Castle Pines Village, Colo. 80104

[*] Notice: The term of this patent shall not extend beyond the expiration date of Pat. No. 5,489,256.

[21] Appl. No.: 596,775

[22] Filed: Feb. 5, 1996

Related U.S. Application Data

[63] Continuation-in-part of Ser. No. 333,360, Nov. 2, 1994, Pat. No. 5,489,256, which is a continuation of Ser. No. 938,629, Sep. 1, 1992, abandoned.

[51] Int. Cl.$^6$ ............................................. A61B 1/00
[52] U.S. Cl. ..................... 600/133; 600/123; 600/153; 600/156
[58] Field of Search ...................... 600/121, 123, 600/125, 133, 153, 156, 157; 604/282; 359/510

[56] References Cited

U.S. PATENT DOCUMENTS

| | | | |
|---|---|---|---|
| 3,043,309 | 7/1962 | McCarthy . | |
| 4,646,722 | 3/1987 | Silverstein et al. | 128/4 |
| 4,737,142 | 4/1988 | Hekele . | |
| 4,869,238 | 9/1989 | Opie et al. | 128/6 |
| 4,878,485 | 11/1989 | Adair | 128/6 |
| 4,984,563 | 1/1991 | Renaud | 128/6 |
| 4,991,564 | 2/1991 | Takahashi et al. | 128/4 |
| 5,125,143 | 6/1992 | Takahashi | 29/237 |
| 5,154,164 | 10/1992 | Chikama | 128/4 |
| 5,167,220 | 12/1992 | Brown | 128/4 |
| 5,188,094 | 2/1993 | Adair | 128/6 |
| 5,188,596 | 2/1993 | Condon et al. | 604/101 |
| 5,193,525 | 3/1993 | Silverstein et al. | 128/4 |
| 5,251,613 | 10/1993 | Adair | 128/6 |
| 5,386,817 | 2/1995 | Jones | 128/4 |
| 5,489,256 | 2/1996 | Adair | 600/133 |

*Primary Examiner*—Richard J. Apley
*Assistant Examiner*—Beverly M. Flanagan
*Attorney, Agent, or Firm*—Fields & Johnson, P.C.

[57] ABSTRACT

An endoscope has a sterilizable, elongated, optical capsule section and a separable, disposable, sterile channel section. The capsule has a window at a distal end in front of an image sensor. Image transmitting electronic cables, connected to the image sensor, extend proximally from the capsule. Light transmitting fibers extend from the window proximally for transmitting light to a site under investigation from a remote light source. The cables and the fibers are housed in a common conduit connected to the proximal end of the capsule. The separable channel section has a distal end removably attached to the capsule and has plurality of longitudinal channels for transmitting fluids or for receiving an operative instrument. A flexible tube is connected to the proximal end of each channel for supplying fluid or for manipulating the operative instrument from a remote location. The separable channel section is disposable after use. The capsule is sterilizable for reuse with another sterile separable channel section on the next patient. The separable channel section can be used with a conventional endoscope. The conventional endoscope can be covered with a sterile sheath to minimize resterilization thereof. An umbilicated balloon catheter or a telescopic catheter can be used to position the endoscope in a passageway. Circumferentially spaced fluid vents can supply jets of gas or liquid selectively to position the endoscope. Alternatively, a magnet can be used for manipulating a capsule with a ferrous housing along a passageway by use of a strong magnet located exteriorly thereof.

6 Claims, 7 Drawing Sheets

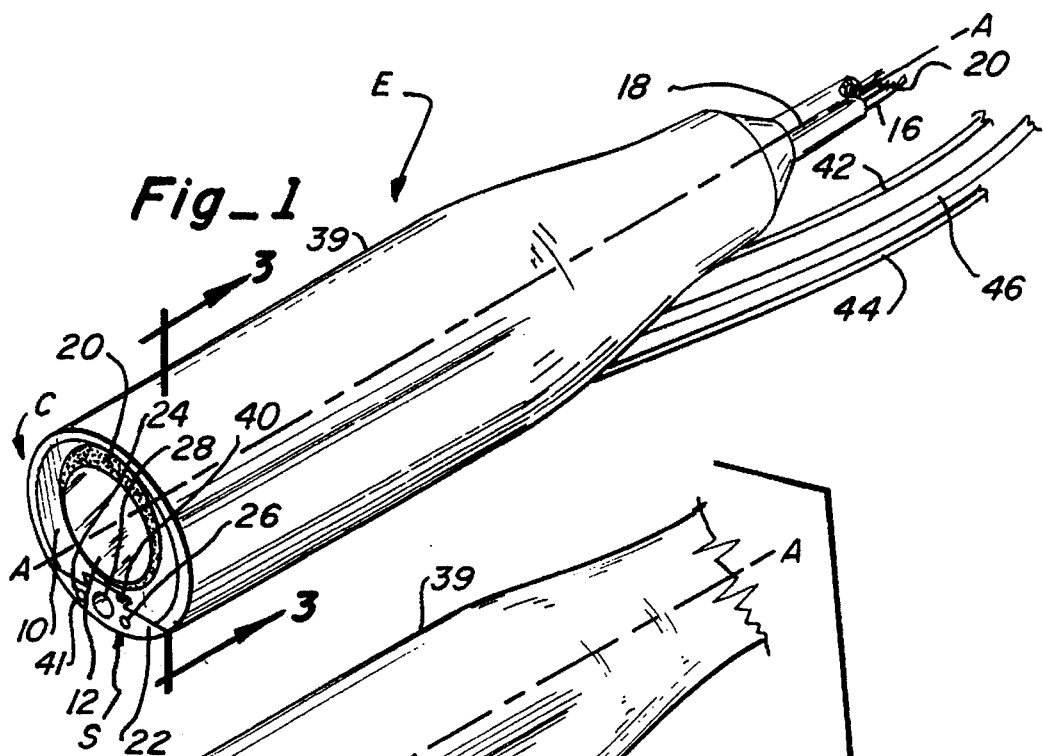
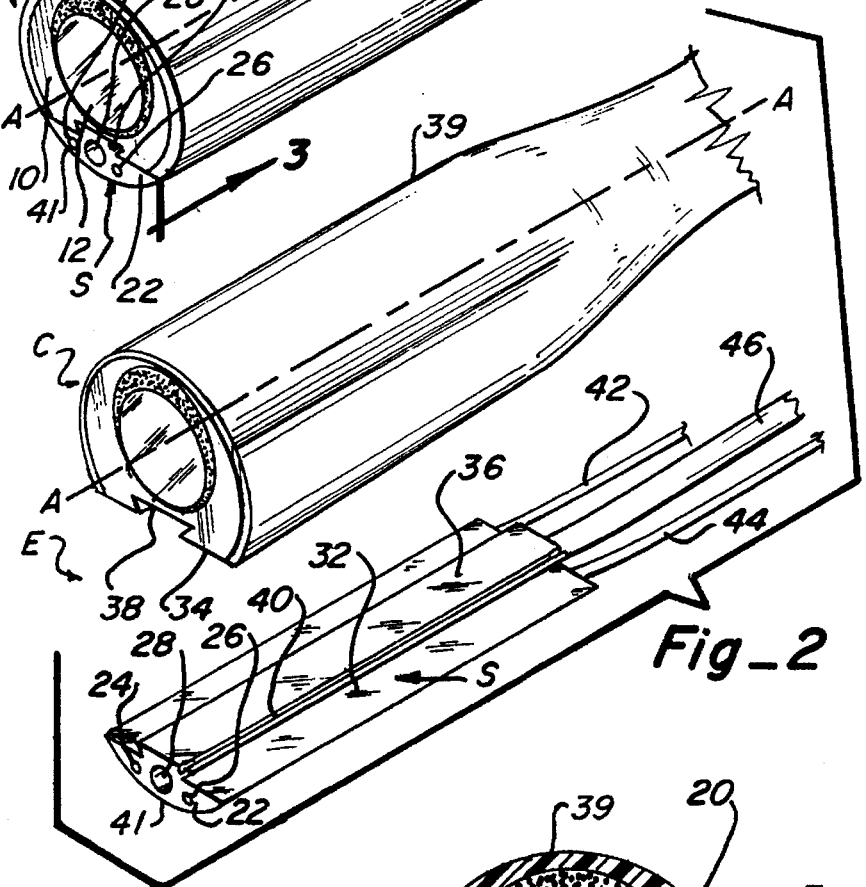
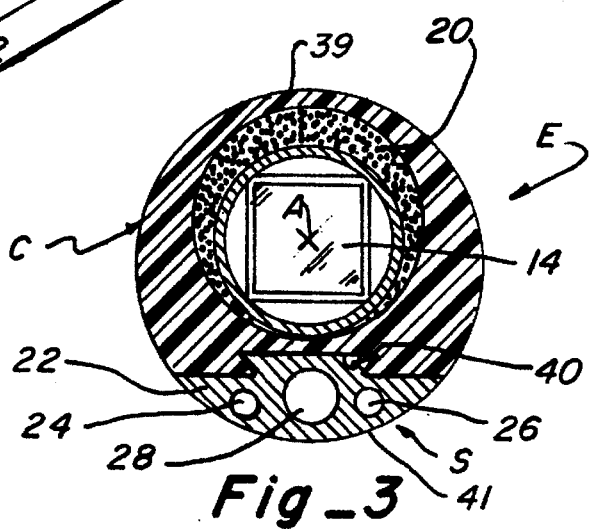

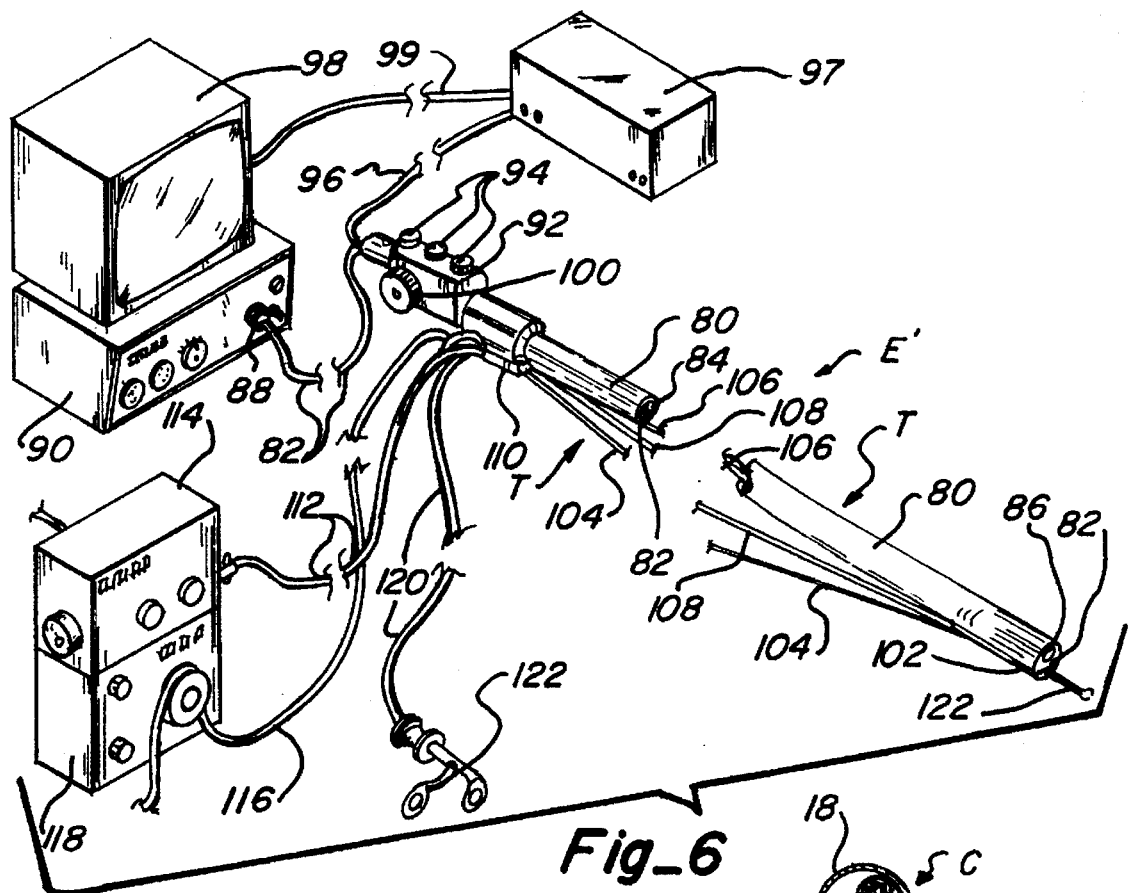
Fig_6
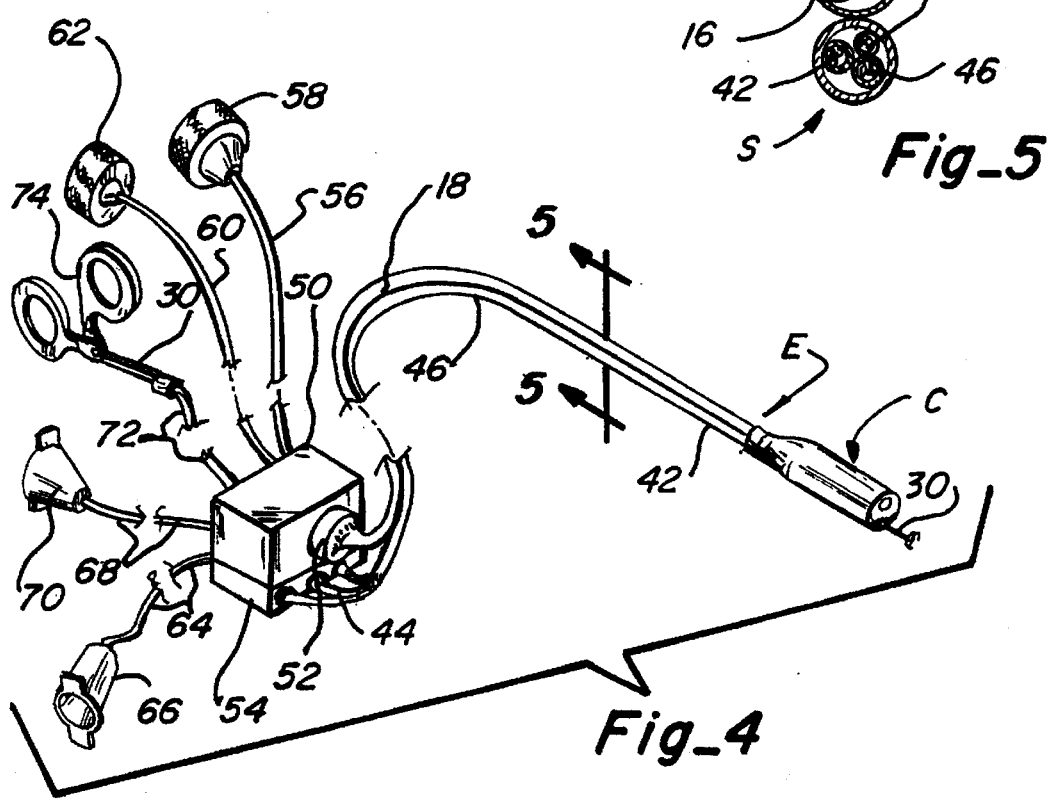
Fig_5
Fig_4

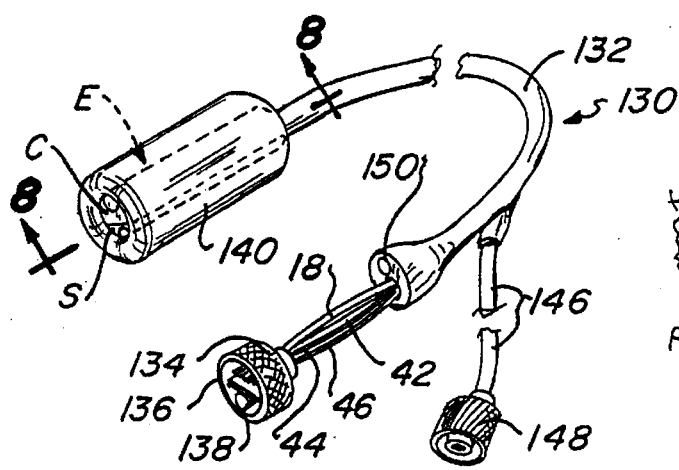
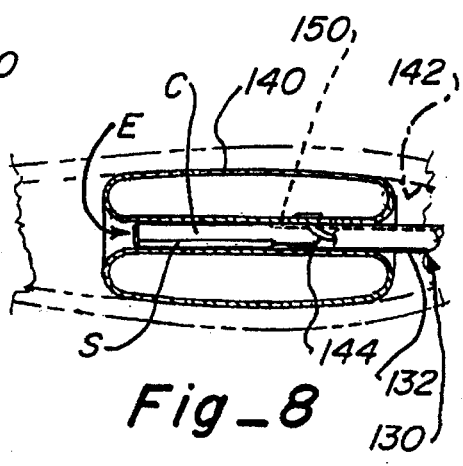
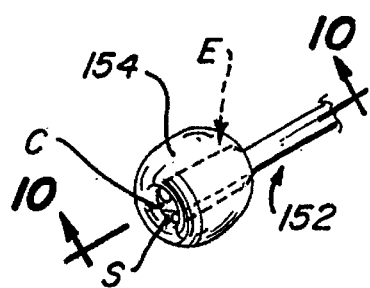
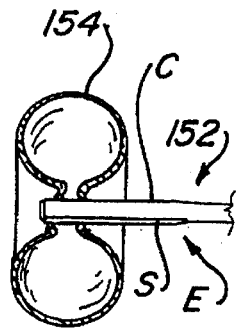
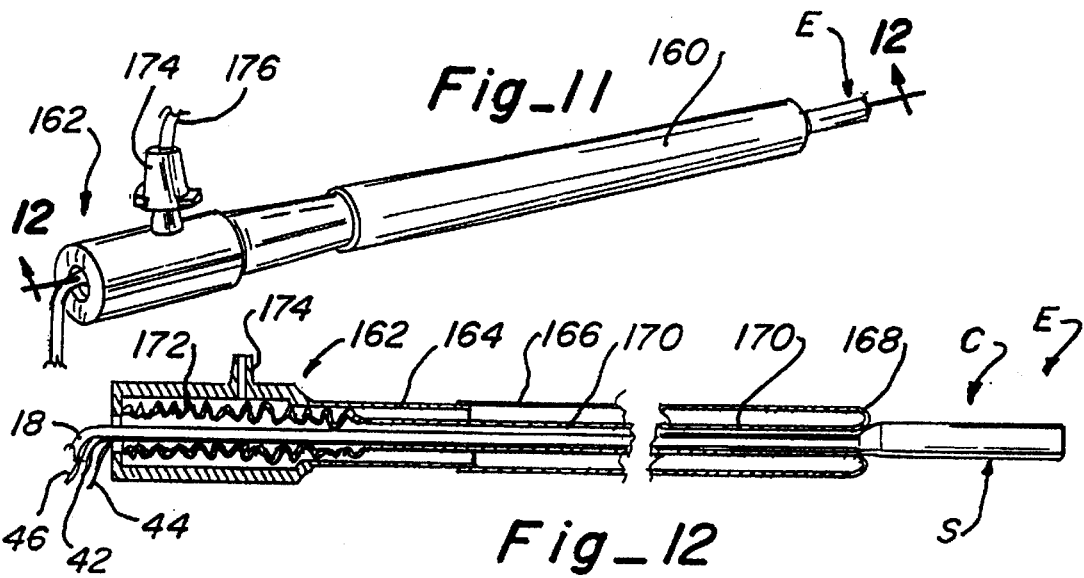

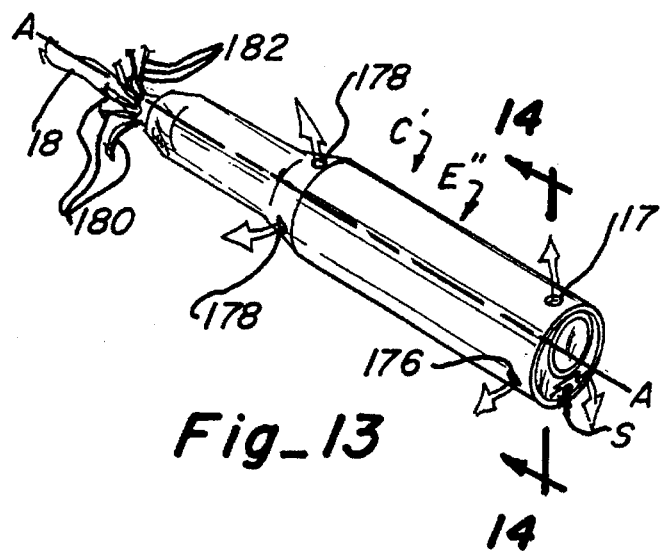
Fig_13
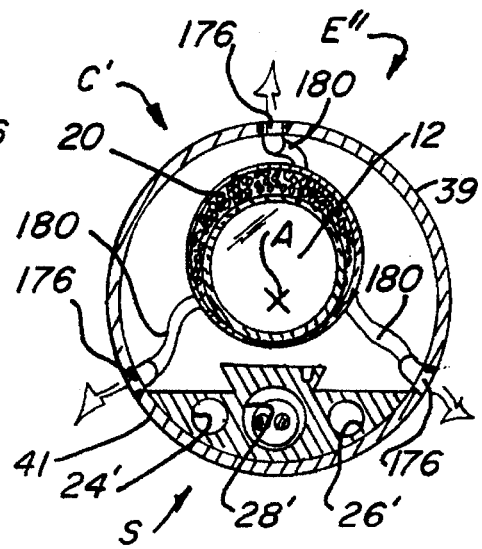
Fig_14
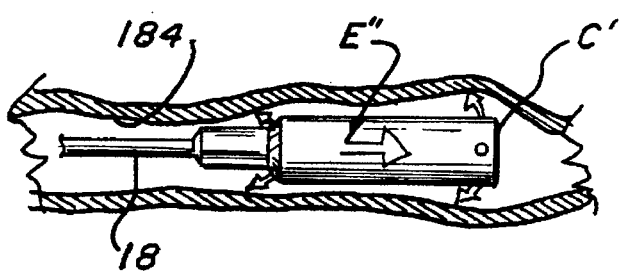
Fig_15
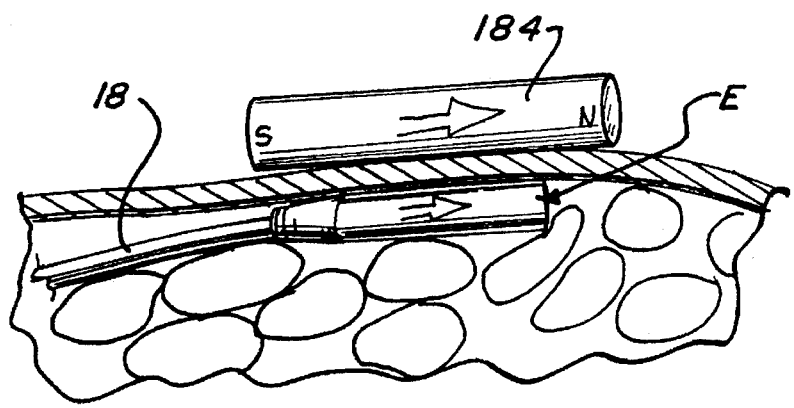
Fig_16

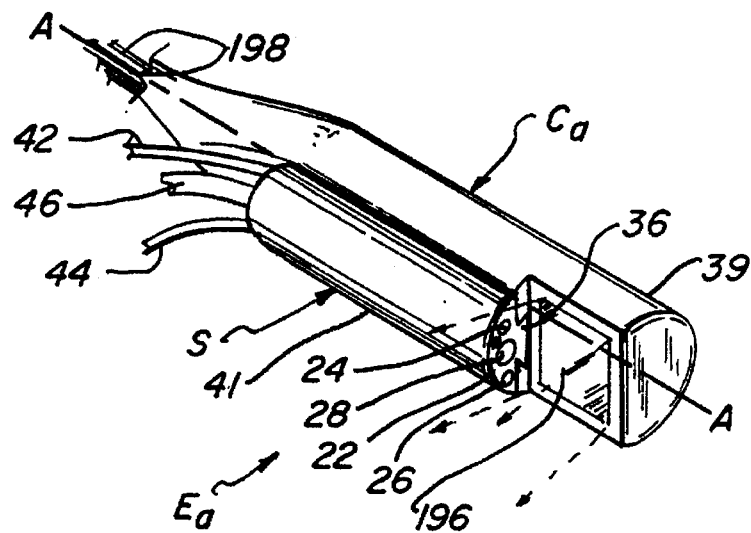
Fig_17
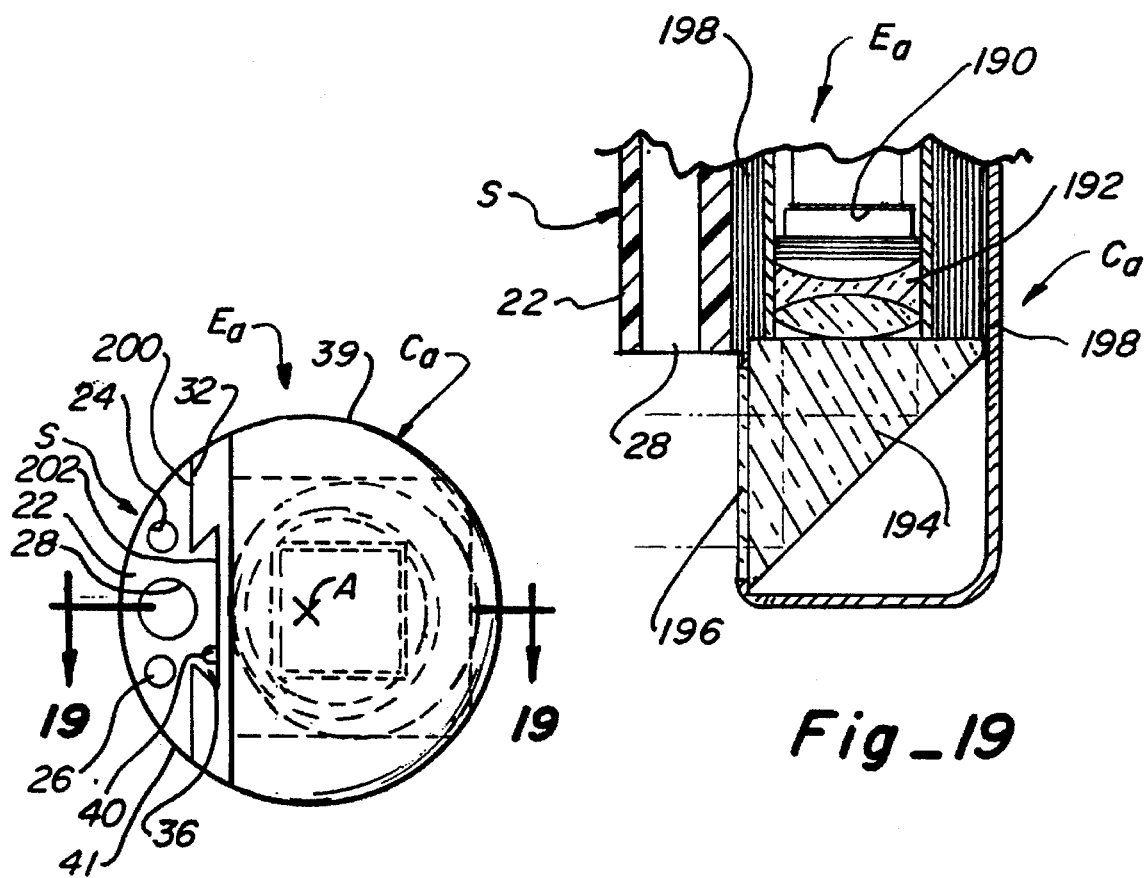
Fig_18
Fig_19

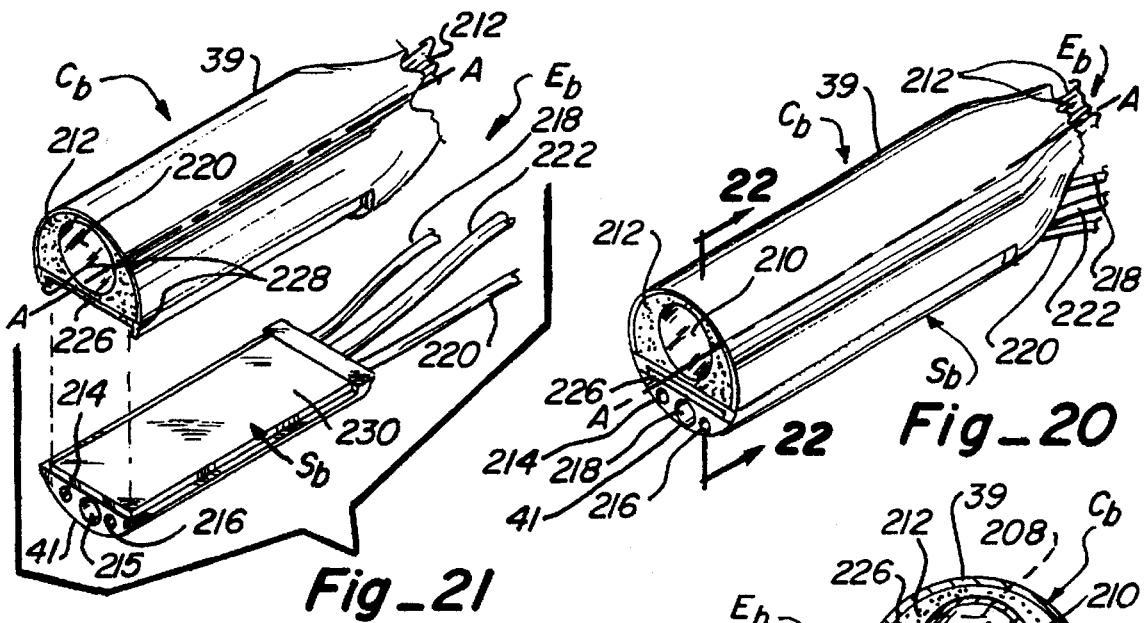
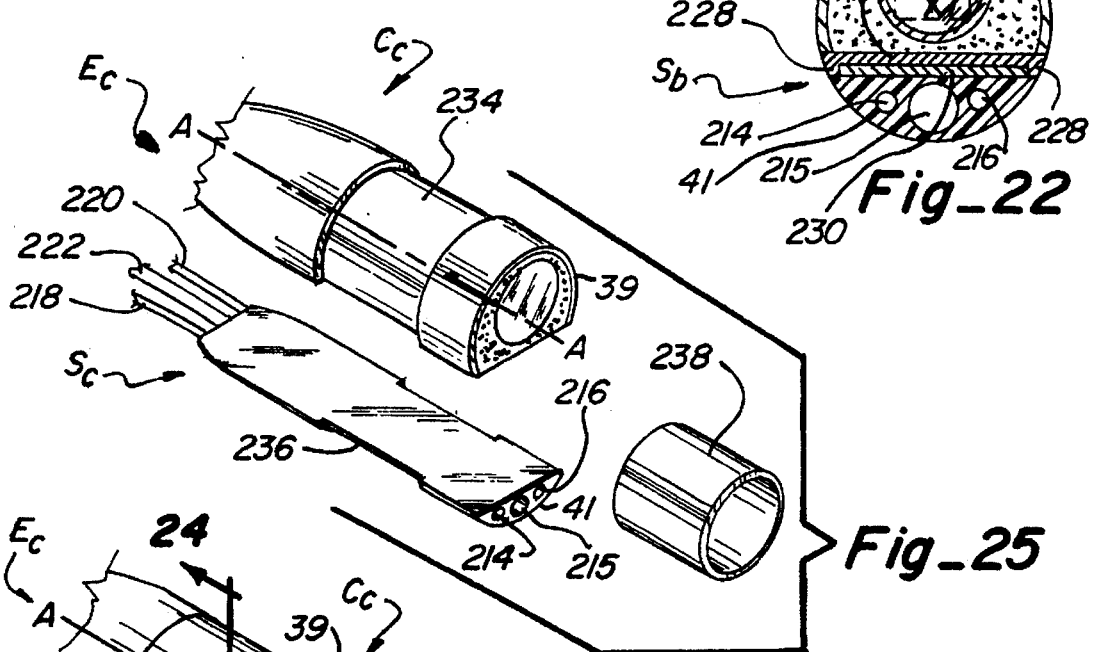
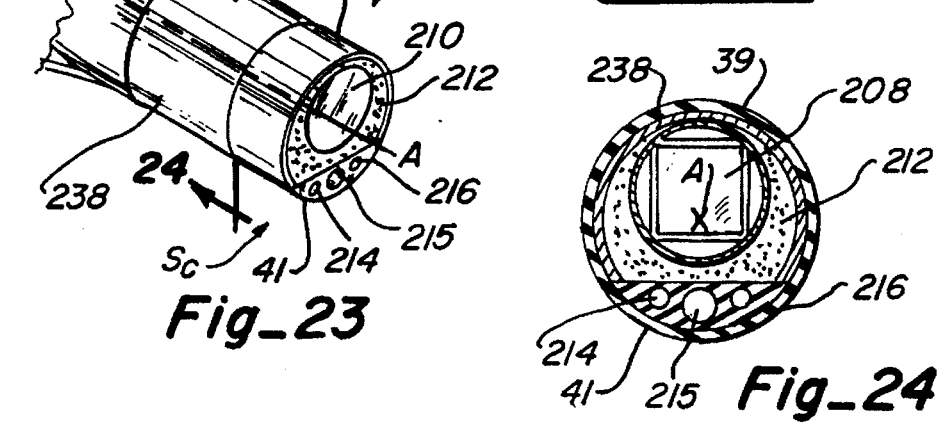

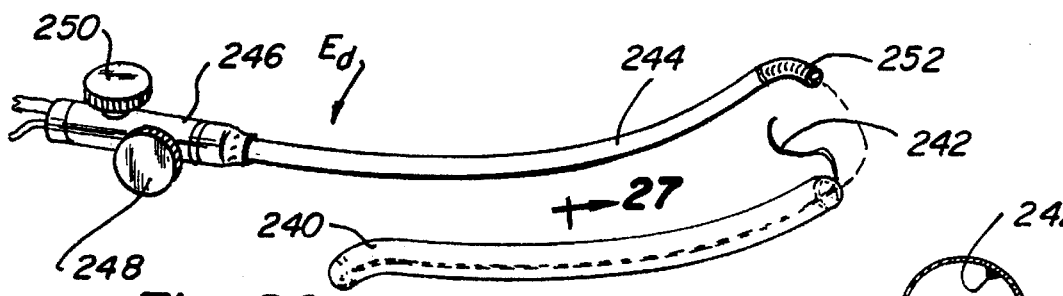
Fig_26 PRIOR ART
Fig_27 PRIOR ART
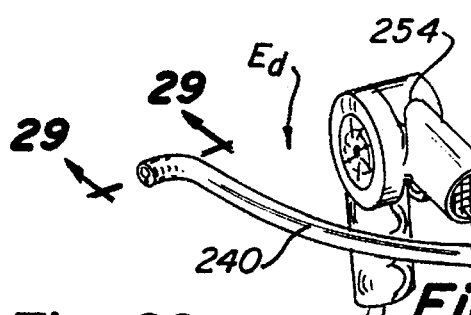
Fig_28 PRIOR ART
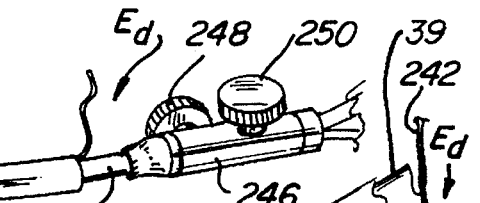
Fig_29 PRIOR ART
Fig_30
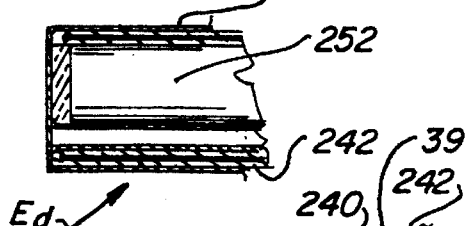
Fig_31
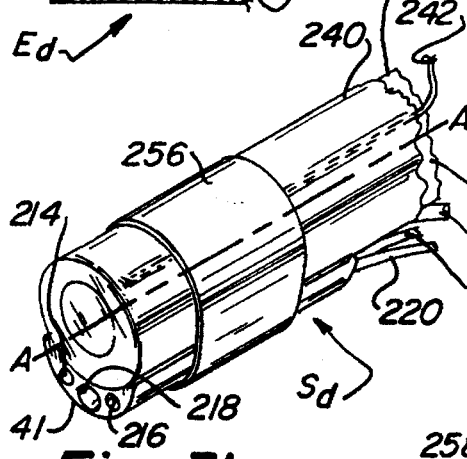
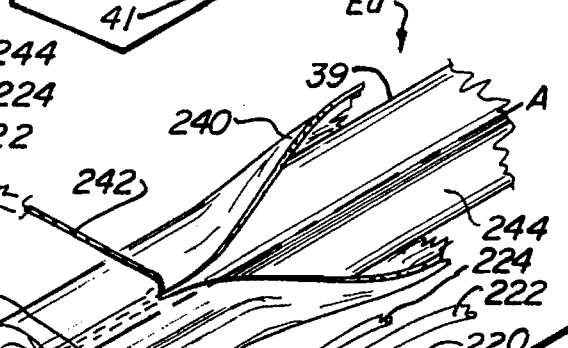
Fig_32

STERILIZABLE ENDOSCOPE WITH SEPARABLE DISPOSABLE TUBE ASSEMBLY

TECHNICAL FIELD

This application is a continuation-in-part of U.S. Patent application Ser. No. 08/333,360 filed Nov. 2, 1994, now U.S. Pat. No. 5,489,256, which is a continuation of U.S. patent application Ser. No. 07/938,629 filed Sep. 1, 1992, now abandoned.

This invention relates to a sterilizable and/or "fluid immersable" endoscope and particularly to a tethered endoscope with a separable disposable tube assembly which can be replaced after each use and resterilization of the endoscope.

BACKGROUND ART

In recent years the popularity of endoscopic surgery has proliferated. This occurred because of the advances in technology which allow smaller and smaller endoscopes to be used, thereby permitting operative procedures to be undertaken in a less invasive manner for the patient than was previously possible. Thus, the patient suffers less trauma, recuperates much more rapidly and experiences less pain and discomfort than with more conventional surgical procedures.

Because of the sophisticated optics and electro-optics contained in modern endoscopes, they generally are very expensive. In order for this expense to be justified, they must be reused with a large number of patients.

Of course, multiple use means that the endoscope must be sterilized or at least disinfected after use with each patient prior to use with the next patient. One protocol for sterilization involves immersing the endoscope in a disinfectant solution for a predetermined period of time. It is also important to flush the channels which carry gases or fluids and those channels which are used for receiving operative instruments. Another protocol is to heat sterilize the endoscope by placing it in an autoclave. However, the optics and electronics of many endoscopes will not permit them to be subjected to heat sterilization. When using the disinfectant, sometimes the endoscope is not placed in the disinfecting solution for a sufficient length of time nor are the channels flushed out completely, because of the urgency to get the endoscope back into service as soon as possible. Over time, the disinfectant solution may loose some of its strength, thereby limiting its effectiveness.

Because of these shortcomings, many studies indicate that transmission of infectious diseases often occurs from one patient to another. By way of example, transmission of salmonella typhi has been reported. In addition, pseudomonas aeruginosa has been linked to improperly sterilized endoscopes. Also, an outbreak of serratia marcescens has been associated with the use of improperly sterilized bronchoscopes. Furthermore, hepatitis B has been transmitted by endoscopes when the endoscopes were processed in an inappropriate manner between patients. Finally, with respect to endoscope used on AID's patients, it has been found that the sterilizing procedures have not always removed contamination of the human immunodeficiency virus (HIV). This list is not exhaustive by any means.

A high-level of disinfection failures among gastrointestinal endoscopes have been noted, as well as failures in bronchoscopes, laryngoscopes and other devices. This may be due to the fact that they are long and narrow and have long and narrow channels which are difficult to clean.

From the foregoing, it is apparent that endoscopes which can be more easily and effectively sterilized are needed.

DISCLOSURE OF THE INVENTION

In accordance with the present invention, an improved endoscope in one configuration has been provided which has a sterilizable optical section and a disposable or throwaway separable channel section or tube assembly. The endoscope includes an elongated capsule, of the size of a medicinal capsule. The capsule includes a substantially cylindrical housing with a transparent window at the distal end thereof, for containing the endoscope optics. An image sensor is mounted adjacent the window within the capsule. An image transmitting cable with multiple conductors each has a distal end connected to the image sensor circuit board and a proximal end connected to a video control unit. From the video control unit signals are transmitted to the video monitor which displays the image in black and white or color. Light transmitting fibers each have a distal end adjacent to the window within the capsule and extends proximally from the capsule for transmitting light to a site under investigation from a remote light source. The separable channel section is removably attached to the capsule in fixed relationship and has at least one longitudinal channel for transmitting fluids or for receiving an operative instrument. A flexible tube is correspondingly connected to the proximal end of the channel for supplying fluid or for manipulating the operative instrument from a remote location. The separable channel section is disposable after use on a patient and the capsule is sterilizable for reuse with another separable channel section on the next patient.

More particularly, the image transmitting filaments and the light transmitting fibers are housed in a common conduit connected to the proximal end of the capsule. Conveniently, the capsule may have a flat relief (i.e., a first substantially planar mating surface) which is engageable with a flat side (i.e., a second substantially planar mating surface) on the separable channel section. The separable section further includes a cylindrical section along its exterior surface with substantially the same radius as the radius of the housing, so that when the capsule and the separable channel section are fastened together, they form the complete cylinder having a substantially circular cross-sectional shape. They may also be configured to have an elliptical cross-sectional shape. The separable channel section may include a plurality of longitudinal channels which comprises at least one fluid transmitting channel and at least one operative channel connected to corresponding tubes for supplying gases or operative instruments from a remote location.

Other means of attachment of the disposable channel section can be utilized. This can include a magnetic attachment or the use of a very strong elastic band. Those schooled in the construction of such disposable tubing devices may envision other methods of holding the separable channel section in the releasable, yet fixed, relationship to the capsule.

This same inventive concept can be used with a conventional endoscope, such as a rigid endoscope or a steerable endoscope having a sterilizable steerable capsule, and a separable channel section releasably connected in a fixed position to the capsule. In this structure, the separable channel section includes a distal housing releasably connected to the distal end of the capsule and a proximal housing releasably connected to the proximal end of the capsule with tubes interconnecting longitudinal channels in each housing. These channels and interconnecting tubes provide passageways through which gases or instruments can be passed.

In another form of the invention, an umbilicated balloon catheter having a tubular wall with an inflatable balloon adjacent the distal end thereof receives the capsule portion of the endoscope of this invention therein so that the capsule is positioned within the distal end of the inflatable balloon so that the balloon is in contact with the body channel that it is passing through rather than the distal end of the endoscope. An inflation conduit is connected to the capsule and extends through the catheter so that the balloon can be inflated while in the body channel or in the passageway. The balloon can either be donut shaped or elongated. Also, the tubular wall of the umbilicated balloon catheter can have a plurality of longitudinal channels for introducing any one of a variety of tools to the site under investigation.

In another form of the invention, a telescopic catheter can be used which has an outer tubular wall folded back upon itself at its distal end. The folded portion of the catheter forms an inner tubular wall telescoped within the outer wall and within a cylindrical housing for storage before expansion. The capsule portion of the endoscope is placed just distally beyond the distal end of the telescopic catheter. The cylindrical housing has means for admitting gas under pressure into the space between the inner and outer tubular walls to expand the catheter so that the distal end moves in a distal direction to push the capsule in the distal direction. This device is generally referred to as a toposcopic catheter developed by the National Institute of Health (NIH).

In a still further embodiment, the capsule can be provided with at least three gas vents equally spaced around the periphery thereof for selectively receiving gas from a gas delivery tube to guide the capsule through the passageway. Alternatively, a strong magnet can be used for manipulating the capsule along a passageway with the magnet located exteriorly thereof.

In another embodiment, the capsule may be configured into a side viewing device, with the optical window facing sideways. Here the image sensor is positioned behind the prism, and the detachable and disposable channel section is stair-stepped to one side and behind the laterally facing window.

By utilizing the endoscope of this invention, a novel method is provided wherein a sterile disposable tube assembly or channel section is attached to a sterilized endoscope having suitable optics for transmitting light to a site under investigation and reproducing an image of the site at a remote location. The endoscope is inserted with the attached tube assembly into a passageway to the desired site. The site is investigated through the endoscope and the necessary operative procedures are carried out through the tube assembly. The endoscope is then removed from the passageway whereupon the separable channel section is separated from the endoscope and thrown away and the endoscope is sterilized. After sterilization a new sterile separable channel section is attached to the sterilized endoscope. This greatly minimized possible cross infection between patients.

Existing endoscopes with built-in operating channels, optics and electronics can be modified for use with a separable channel section. This is a accomplished by encapsulating the entire steerable endoscope in a translucent sterile covering of thin, heat shrinkable plastic tubing closed at the distal end. This condom shaped covering can be placed over the endoscope and heat shrunk down to a very tight fitting covering encasing and sealing all of the endoscope including the hard to clean operating channels therein. This effectively isolates the endoscope in a sterile sheath and bars any cross contamination to the patient from the endoscope.

The separable channel section is then mounted onto the sheath enclosed steerable endoscope adjacent the distal end thereof with an elastic band holding it in proper position. The separable channel section has a concave mating surface to fit snugly around the rounded body of the steerable endoscope which serves as a complementary convex mating surface. The sheath has incorporated therein a nylon string extending longitudinally therealong which allows easy tearing of the sheath after use for removal. A new sterile sheath can be heat shrunk onto the endoscope for use on the next patient.

The endoscope of this invention, because of its very small size substantially reduces the size and weight compared to conventional devices resulting in considerably more comfort for the patient. One of the most traumatic experiences for patients is the insertion of very large diameter and very heavy endoscopes into the colon, stomach or bronchial tree.

With this last-described apparatus, a method has been provided for utilizing a separable channel section on a conventional endoscope. The method includes placing a sterile heat shrinkable sheath on the body of the endoscope and applying heat to the sheath to shrink it into sealing engagement with the endoscope body. The separable channel section is releasably attached to the distal end of the endoscope body around the sheath in a fixed position. The operative site is investigated and the necessary, operative procedures are performed. The endoscope is then removed, the separable channel section is separated from the endoscope and thrown away and the sheath is removed from the endoscope and thrown away.

BRIEF DESCRIPTION OF THE DRAWINGS

FIG. 1 is a perspective view of an endoscope having a sterilizable optical capsule section with a disposable separable tube assembly or disposable separable channel section;

FIG. 2 is a fragmentary exploded view of the endoscope of FIG. 1;

FIG. 3 is an enlarged vertical section, taken along line 3—3 of FIG. 1;

FIG. 4 is a perspective view of the endoscope of FIG. 1 connected through a control member to suitable gas supplying and instrument supplying channels;

FIG. 5 is an enlarged vertical section, taken along line 5—5 of FIG. 4, showing the interior construction of the conduits for the capsule and the separable channel section;

FIG. 6 is a perspective view of a steerable electronic endoscope having a separable channel section;

FIG. 7 is a perspective view showing the use of the invention in an umbilicated balloon catheter;

FIG. 8 is an enlarged horizontal section, taken along line 8—8 of FIG. 7, showing details of the balloon construction;

FIG. 9 is a perspective view of the endoscope of this invention used with an alternative umbilicated balloon catheter;

FIG. 10 is an enlarged horizontal section, taken along line 10—10 of FIG. 9, showing details of the balloon construction;

FIG. 11 is a perspective view of a telescopic catheter (also known as toposcopic catheter) used with the endoscope of this invention;

FIG. 12 is an enlarged longitudinal section, taken along line 12—12 of FIG. 11, showing details of the telescopic catheter;

FIG. 13 is a perspective view of an alternative endoscope having gas vents for guiding it along a bodily passageway;

FIG. 14 is an enlarged vertical section, taken along line 14—14 of FIG. 13, showing the gas passageways connected to the vents;

FIG. 15 is a section through a bodily passageway showing the catheter of FIG. 13 therein;

FIG. 16 is a section through the intestines of a patient showing the endoscope of this invention being drawn therealong by means of a strong magnet;

FIG. 17 is a fragmentary perspective view of another still further embodiment of the endoscope of this invention utilizing a prism for side viewing;

FIG. 18 is an enlarged end view of the endoscope of FIG. 17;

FIG. 19 is a fragmentary horizontal section, taken along line 19—19 of FIG. 18 showing further details of the endoscope construction;

FIG. 20 is a fragmentary perspective view of another alternative embodiment of the endoscope wherein the separable channel section is magnetically attached;

FIG. 21 is an exploded view of the endoscope of FIG. 20;

FIG. 22 is an enlarged vertical section, taken along line 22—22 of FIG. 20;

FIG. 23 is a fragmentary perspective view of yet another embodiment wherein the sterilizable capsule and the separable channel section are held together by an elastic band;

FIG. 24 is an enlarged vertical section, taken along line 24—24 of FIG. 23;

FIG. 25 is a fragmentary exploded view of the endoscope of FIG. 23;

FIG. 26 is a perspective view of a prior art steerable endoscope having a removable sterile sheath;

FIG. 27 is an enlarged section, taken along line 27—27 of FIG. 26, showing the construction of the sheath;

FIG. 28 is a perspective view of the prior art endoscope with the sheath in place, showing it being heat shrunk onto the endoscope;

FIG. 29 is an enlarged fragmentary horizontal section, taken along line 29—29 of FIG. 28, showing the heat shrunk sheath in place on the end of the endoscope;

FIG. 30 is a fragmentary exploded perspective view of the end of the endoscope of FIG. 26 with the heat shrunk sheath in place and showing the separable channel section and an elastic band for holding it in place;

FIG. 31 is a fragmentary perspective view of the apparatus of FIG. 30 when assembled; and FIG. 32 is an exploded fragmentary perspective view of the endoscope assembly being dissembled after use.

BEST MODE FOR CARRYING OUT THE INVENTION

In accordance with one form of this invention, a tethered endoscope E is provided as best seen in FIGS. 1–4 which includes a sterilizable capsule C to which a disposable separable channel section S is releasably attached. Capsule C, which is easily sterilizable by heat in an autoclave, by gas sterilization or by dipping it in a disinfectant, has a window 10 at the distal end thereof. Positioned directly behind the window is a lens system 12 for focusing an image at a site under investigation on to an image receptor, such as CCD chip 14. It will be understood that other types of image receptors, such as a CID and MOS device or coherent optic fibers for guiding an image to a remotely located camera can be provided. However, under present technology, the CCD chip is the only electronic receptor of sufficiently small size to be placed in a capsule of the type contemplated by this invention. In this regard, the capsule is the size of a medicinal capsule, being 0.7 cm in diameter and 1.5 cm in length. Thus, it is small enough to be swallowed by a patient or otherwise introduced into small bodily passageways. The CCD is connected to electronic cable 16, shown in FIG. 1 which extend through a conduit 18 to a remote location, as will be more fully described below. The CCD is at least partially surrounded by optical fibers 20 for transmitting light to the operative site for viewing by means of the CCD 14. These optical fibers also extend through conduit 18. Conveniently, conduit 18 will have a diameter of only 1/16 of an inch or smaller. This structure can be sterilized easily by immersing it in a disinfectant solution or by placing it in an autoclave for heat sterilization or by using ethylene oxide for gas sterilization.

Conveniently, the separable channel section S is removably connectable to capsule C in a fixed position and includes a channel member 22 having a plurality of channels, such as channels 24 and 26 for introduction of gas, such as carbon dioxide gas, or for drawing a suction to remove fluid or tissue from the operative site. Also, one channel could be used to direct fluid under pressure to clean the end of the optics to assure precise viewing. Another channel could be used to direct a flow of warm gas over the optics for drying the optics. A larger central channel 28 is provided through which an operative tool, such as tool 30 shown in FIG. 4, can be provided. Although the tool is illustrated as being forceps, it will be understood that other instruments may be utilized. Conveniently, separable channel section S has a flat surface 32 which engages a flat surface 34 of capsule C. Channel section S further includes a central longitudinally extending guide or key 36 which is engageable in a longitudinal guideway or keyway 38 formed in flat surface 34 on capsule C. In order to better illustrate how capsule C and separable section S are attached, it will be understood that the shape of capsule C is defined by an exterior surface which includes surface 34, keyway 38 and outer edge 39. Similarly, separable channel section S has a shape defined by an exterior surface which includes flat 32, key 36 and arcuate outer edge 41. Common to all the embodiments disclosed herein is that when capsule C attaches to section S, the exterior surfaces of each element form a substantially circular or oval cross section. Central axis A—A is provided showing the appropriate geometric center of the cross-sectional shapes wherein the attachment of the capsule C to the separable section S results in either the substantially circular (e.g. FIG. 1) or oval (FIG. 31) shape. In use, a sterilized capsule is attached to a new sterile separable channel section S whereupon endoscope E can be introduced into a passageway of the body of a patient by one of many methods to be described, so that suitable investigative and/or operative procedures can be undertaken.

Once the procedures are completed, the endoscope can be withdrawn. Section S is then separated from capsule C and thrown away and the capsule is sterilized by immersion in disinfectant or by placing it in an autoclave for heat sterilization or gas sterilization over an appropriate period of time. In this manner, the expensive optical portion of the endoscope E is preserved for multiple uses whereas the inexpensive, easily contaminated and difficult to sterilize separable channel section S can be separated from capsule C and thrown away.

Conveniently, separable channel section S can be provided with an additional channel 40 as shown for the introduction of a guide wire which has been previously positioned in the body of the patient by a catheter in a conventional manner. Thus, after removal of the catheter over the guide wire, the capsule can be placed on to the guide wire and slid therealong over channel 40 until it is also properly positioned.

Conveniently, tubes are connected to the proximal end of section S which are in communication with the channels therein. For example, a tube 42 is connected to channel 24 and a tube 44 is connected to channel 26. Similarly, a larger tube 46 is connected to larger operating channel 28. Each tube can be connected to a suitable connector, not shown, for introducing an appropriate fluid or instrument.

As best seen in FIG. 4, an alternative arrangement is shown wherein the conduit 18 extends distally to a housing 50 to which it is releasably connected by fitting 52. Conveniently, the housing 50 has a removable section 54 to which tubes 42, 44 and 46 are connected. On the other side of housing 50, a conduit 56 is provided for connecting the light fibers to a suitable source of light through fitting 58. Similarly, a conduit 60 is provided for conducting the electrical signals to an image processing device through connector 62.

Similarly, connected to the back side of removable section 54 is a tube 64 which is in further communication with tube 42 and is connected to a luer lock 66. A second tube 68 is in fluid communication with tube 44 and is provided with a luer lock 70. A third tube 72 is in communication with operating tube 46 and is adapted to receive an instrument, such as instrument 30, which has a handle 74 connected directly to it.

The same inventive concepts just described can be applied to a steerable endoscope E', as best seen in FIG. 6. This endoscope includes a barrel 80 with light fibers 82, for providing light to a site under investigation, and electronic cables 84 attached to a CCD (not shown) for transmitting an image which is viewed through lens 86. As illustrated, light fibers 82 are connected through a fitting 88 to a light source 90. The CCD is connected to a camera 92, having controls 94, and supplying an image through conduit 96 to a video control unit 97 and then to video monitor 98 via cable 99. The steering mechanism within barrel 80 is controlled, as by knob 100 and may be of the type shown in my U.S. Pat. No. 5,325,845 entitled "Steerable Sheath For Use With Selected Removable Optical Catheter", or any other well-known steering device. In an alternative configuration, the imaging system of the steerable endoscope may be a coherent optical fiber bundle instead of a CCD.

As seen in FIG. 6, a separable channel section 102 is removably connected to the distal end of barrel 80 in the same manner in which separable section S is attached to capsule C in FIG. 2. Section 102 has a plurality of longitudinal channels, such as three, which are connected to a vacuum hose 104, a fluid hose 106 and an instrument tube 108. These are connected to a proximal housing 110 which also is of similar construction to separable channel section S, shown in FIG. 2, and is releasably connected to barrel 80 in a similar manner. Housing 110 includes longitudinal channels, one of which respectively communicates vacuum hose 104 with vacuum hose 112. That is, hose 112 is attached between the proximal end of housing 110 and a vacuum pump 114. Another channel in housing 110 communicates fluid hose 106 with fluid hose 116 which is connected to a fluid pump 118. A third central channel in housing 110 communicates instrument tube 108 with instrument tube 120 for receiving an operative instrument, such as forceps 122.

As with endoscope E, steerable endoscope E' can be initially sterilized in a sterilizing solution or by heating it in an autoclave or by gas sterilization for a suitable period of time to kill any viruses or bacteria remaining on the endoscope from its previous use. The endoscope can then be used in a conventional manner and, after use, separable channel section 102 can be separated from the endoscope and thrown away. The endoscope E' can be resterilized by putting it in an autoclave or by soaking it in a suitable disinfectant. Thereafter, endoscope E' can be reconnected to a new sterile separable channel section for reuse.

Various methods are available for introducing endoscope E into the body. As previously explained, it is of very small size, being approximately the same size as a medicinal capsule. Thus, it can be swallowed and if necessary a metallic weight can be imbedded into the terminal end to aid in propulsion of the capsule through the gastrointestinal track.

A second method of insertion and propulsion is by use of an umbilicated balloon catheter 130, of the type shown in FIGS. 7 and 8, in which endoscope E can be preloaded. Preloading is of great help to the endoscopist because it saves him or her the time and trouble of inserting the devices over long distances inside exceptionally long operating channels. As can be seen in FIG. 7, conduit 18 as well as tubes 42, 44 and 46 pass through a central passageway 132 in the catheter and are attached to a connector 134 which has an optics portion 136 and a separable tube connector 138 which can be attached to the appropriate instrumentation, as previously described. The distal end of catheter 130 is provided with an inflatable balloon 140 which can be used to center the catheter in a body passageway 142 as best seen in FIG. 8. As shown, the distal end of the endoscope E is positioned within the distal end of the balloon 140 so that when the catheter 130 is introduced through a body passage, the distal end of the balloon 140 acts as a cushion and the endoscope E does not come into contact with body tissue. The balloon provides a very safe non-traumatic guide when used in the bowel or colon. When lubricated, the balloon offers little resistance to the passage of the catheter to its desired location. The balloon is inflated through a tube 144 which is connected to a gas supply tube 146 whose proximal end is connected to a suitable connector 148. The umbilicated balloon catheter 130 can be provided with an additional channel 150 for introduction of a guide wire (not shown) to introduce umbilicated catheter 130 through a trochar (not shown) to the desired location within a patient's body in a conventional manner.

Another umbilicated balloon catheter 152 is shown in FIGS. 9 and 10 wherein the balloon 154 has a generally donut configuration, because it has less contact surface with the passageway it can be more easily manipulated therealong. As with the catheter 130 shown in FIGS. 7 and 8, the distal end of the balloon 154 extends beyond the distal end of the endoscope E to provide the necessary cushioning effect.

The endoscope E can also be inserted by use of a telescopic catheter 160, as shown in FIGS. 11 and 12. The generally cylindrical housing 162 is provided which has a distal cylindrical portion 164 to which an outer tubular wall is securely attached. This wall is folded back upon itself to create a distal end 168 and to form an inner tubular wall 170 which is fan folded within housing 162 to form a folded proximal end 172, as shown in FIG. 12. This catheter 160 can be preloaded with endoscope E, having capsule C extending beyond the distal end thereof and conduit 18 and tubes 42, 44 and 46 extending through the inner tubular wall 170 and out the proximal end, as shown. Housing 162 has a gas inlet 174 to which a gas supply hose 176 is connected. When gas is introduced under pressure, the distal end 168 of the catheter will be pushed in a distal direction, thereby moving capsule C in that same distal direction. Thus, the capsule can be moved into its appropriate location by the expansion of telescopic catheter 160.

An alternative form of endoscope E" is illustrated in FIGS. 13–15. This endoscope has a capsule C' with circumferentially and equally spaced fluid vents 176. A similar set of fluid vents 178 are provided adjacent the proximal end thereof. Fluid vents 176 are supplied with a gas or liquid through supply tubes 180, whereas fluid vents 178 are supplied with a gas or liquid through supply tubes 182. When the endoscope E" is introduced into a bodily passageway, such as passageway 184, shown in FIG. 15, the fluid can be selectively controlled through remote control valves (not shown) connected to supply tubes 180 and 182 so that jets of gas or liquid can be ejected selectively through any one of vents 176 or vents 178 in any combination so as to manipulate and guide the endoscope through the passageway.

FIG. 16 shows the use of endoscope E within the intestines of patient wherein the endoscope is moved along the desired path by a strong magnet 185. An example of such a magnet is one made of Samarium Cobalt which is available through the Hitachi Corporation of Midland, Mich. U.S.A. In this application, the endoscope housing is made of ferrous material.

A further embodiment is shown in FIGS. 17–19 wherein an endoscope $E_a$ is provided which has a capsule $C_a$ with a prism therein for viewing at right angles the instruments introduced through separable section S. In this regard, capsule $C_a$ has a CCD chip 190 mounted adjacent the distal end thereof for receiving an image projected through a lens system 192 mounted distally thereof. Attached to the lens system is a prism 194 for viewing an image projected through a window 196, as shown. Optical fibers 198 surround the CCD and project light onto the operative site by means of prism 194.

Separable channel section S is identical to section S of FIG. 1. It has a flat 32, which engages a flat surface 200 on capsule $C_a$, and a central longitudinally extending guide or key 36 which is engageable in a longitudinal guideway or keyway 202 formed in flat surface 200 on capsule $C_a$. Guideway 36 can be provided with an additional channel 40 for introduction of a guide wire, as best seen in FIG. 18.

Yet another embodiment is shown in FIGS. 20–22, wherein an endoscope $E_b$ has a sterilizable capsule $C_b$ to which a separable section $S_b$ is attached by means of a magnetic strip. Capsule $C_b$ is substantially identical to capsule C of FIG. 1. The capsule includes a CCD chip 208 having a lens 210 for focusing an image at the operative site thereon. Light transmitting fibers 212 are positioned around the CCD and lens structure for directing light to the operative site. Separable channel section $S_b$ has fluid passageways 214 and 216 with an instrument passageway 215 of larger size therebetween. Passageway 214 is connected to a tube 218; passageway 216 is connected to tube 220 and instrument passageway 215 is connected to tube 222. The mating surface of capsule of $C_b$ is provided with a ferrous metal plate 226 having depending flanges 228 on opposite sides thereof. Separable section $S_b$ has a magnetic strip 230 which is held in place against plate 228 by magnetic attraction and is sized to fit within the flanges 228 to hold the separable section in a fixed but removable position.

Another embodiment is shown in FIGS. 23–25 wherein an endoscope $E_c$ has a capsule $C_c$ and a separable channel section $S_c$ which are held together by an elastic band. Capsule $C_c$ is substantially identical to capsule $C_b$ in the previous embodiment except that it includes a recess 234 around its periphery. Section $S_c$ also has a corresponding recess 236 around its periphery for receiving and positioning an elastic band 238, thereby holding capsule $C_c$ and Section $S_c$ together in a fixed position during use.

A final embodiment is shown in FIGS. 26–32 wherein a conventional prior art steerable endoscope $E_d$ is provided with a sterile sheath 240 which is made of heat shrinkable material which is transparent and has a pull string 242 extending substantially the full length of the sheath for ripping it open after use, as will be explained more fully below. The steerable endoscope $E_d$ has a flexible body portion 244 whose proximal end is connected to a handle 246 having controls 248 and 250 for manipulating the distal end 252. It also includes one or more channels, not shown, which are used for passage of fluids and instruments when the endoscope is used in the conventional manner.

When the conventional prior art endoscope is to be used in accordance with this invention, the sterile sheath 240 is placed over the end of the endoscope and drawn up over body 244, thereby covering the channels and body, and heat is applied thereto, as by a forced air dryer 254, which causes the sheath 240 to seal tightly around endoscope body 244. The sheath 240 is transparent so as not to interfere with light or image transmission through the encased endoscope.

Next, a separable section $S_d$ is attached to the distal end 252 of endoscope $E_d$ over the sheath 240 and is fixedly held in place, as by a sterile elastic band 256. Separable section $S_d$ is similar to the separable sections of the previous embodiments except that it has a concave surface 258 which mates with the outer surface 39 of distal end 252 of endoscope $E_d$. When assembled, the apparatus will have the configuration shown in FIG. 31 whereupon it can be inserted through a body passageway and used for its intended purpose. After use, band 256 is removed, as shown in FIG. 32, and the sheath 240 is removed by pulling on string 242 which longitudinally rips the sheath apart so that it can be separated from endoscope $E_d$. Thus, the present application can be adapted for use with conventional endoscopes without modification thereof. This provides a means and method of reusing a conventional endoscope without encountering the expense, time delay and uncertainty associated with conventional resterilization procedures. Although a steerable endoscope has been illustrated and described, the sheath can be used also with a conventional rigid endoscope.

From the foregoing, the advantages of this invention are readily apparent. An endoscope has been provided which is of very small size having a sterilizable optical section and a disposable sterile separable channel section which is removably but fixedly attached to the capsule so that after initial use, the separable channel section can be separated from the optical section and thrown away. The capsule then is resterilized by heating it in an autoclave or by immersing it in a sterilizing solution for a suitable length of time. After the capsule is resterilized, a new sterile separable channel section can be attached to the resterilized capsule and the endoscope reused. The device can be end viewing or, by use of a prism, side viewing. A similar structure can be provided on a steerable endoscope wherein the channel section is separable from the capsule which is steerable. Additionally, the endoscope, because of its small size can be introduced into the body by swallowing since it is no larger than a medicinal capsule. Other ways of introducing the device are by umbilicated balloon catheters which offer almost no resistance in bodily passageways and serve to center the catheter within the passageway and protect the body tissue. Another alternative is the use of a telescopic catheter for placement of the endoscope in the desired location. The endoscope can also be provided with fluid vents which are selectively supplied with fluid to steer the endoscope as it is moved into a bodily passageway. Finally, a strong magnet can be used outside the bodily passageway for pulling the endoscope, having a ferrous housing, into the desired location. In other embodiments, a separable channel section can be fixedly attached to the capsule by an elastic band or magnetically. Finally, the separable channel section can be used with a conventional endoscope which has been sealed in a sterile sheath.

This invention has been described in detail with reference to particular embodiments thereof, but it will be understood that various other modifications can be effected within the spirit and scope of this invention.

I claim:

1. An improved endoscope comprising:

a first segment comprising a substantially cylindrical capsule including distal and proximal ends and a first curved exterior surface, said capsule further including a transparent window at said distal end and a first substantially planar mating surface opposite said first exterior surface;

an image sensor mounted adjacent said window and within said first segment;

at least one image transmitting cable connectable to said image sensor and extending proximally from said first segment for transmitting an image signal from said image sensor to a video control unit and then to a remote image display device;

at least one light transmitting fiber having a distal end adjacent said window within said first segment and extending proximally from said first segment for transmitting light to a surgical site from a remote light source;

a second segment comprising a separable disposable channel section having at least one longitudinal opening for transmitting fluids or for receiving an operative instrument and further having a second curved exterior surface and a second substantially planar mating surface opposite said second exterior surface, said second substantially planar mating surface being releasably attachable to said first substantially planar mating surface of said capsule such that there is formed a substantially planar interface between said first and second segments;

an umbilicated balloon catheter having a tubular wall with an inflatable balloon adjacent a distal end thereof, said distal end of said balloon catheter being positioned distally beyond said distal end of said first segment; and wherein said first and second segments, when attached along said first and second mating surfaces, together form a cylindrical endoscope having a substantially contiguous smooth curved exterior surface and a substantially circular cross-sectional shape, such that after use on a patient, said second segment is disposable while said first segment is sterilizable for reuse with a new second segment on another patient.

2. The endoscope, as claimed in claim 1, wherein:

said first substantially planar mating surface comprises a longitudinal keyway having a recessed portion, and said second substantially planar mating surface includes a longitudinal key which is engageable with said longitudinal keyway.

3. The endoscope, as claimed in claim 1, wherein:

said second segment is shaped such that said first segment and said second segment, when attached have a substantially common radius as defined from a central axis extending through the approximate geometric center of said endoscope.

4. The endoscope, as claimed in claim 1, further including:

at least one longitudinal opening extending longitudinally within said tubular wall in fluid communication with said balloon for inflation of said balloon to center said endoscope in a passageway of a patient into which said catheter has been introduced to protect the passageway when said catheter is moved along the passageway.

5. The endoscope, as claimed in claim 1, wherein:

said umbilicated balloon catheter has a substantially cylindrical shape.

6. The endoscope, as claimed in claim 1, wherein:

said umbilicated balloon catheter has a donut-like shape.

* * * * *